United States Patent [19]

Florkowski et al.

[11] Patent Number: 5,287,731
[45] Date of Patent: Feb. 22, 1994

[54] THERMO-OXIDATION ENGINE OIL SIMULATION TESTING

[75] Inventors: Dennis W. Florkowski, Southfield; Theodore Selby, Midland, both of Mich.

[73] Assignee: Chrysler Corporation, Highland Park, Mich.

[21] Appl. No.: 74,529

[22] Filed: Jun. 11, 1993

[51] Int. Cl.$^5$ ............................................. G01N 11/00
[52] U.S. Cl. .................................. 73/53.05; 73/61.62; 73/865.5; 422/53; 436/6; 436/60
[58] Field of Search ............... 73/53.05, 61.62, 865.5; 422/53, 68.1; 436/6, 60

[56] References Cited

U.S. PATENT DOCUMENTS

| | | | |
|---|---|---|---|
| 2,819,611 | 1/1958 | Shellard et al. | 73/53.05 |
| 3,200,638 | 8/1965 | Haut | 73/53.05 |
| 3,318,667 | 5/1967 | Fabuss et al. | 73/61.62 X |
| 3,552,189 | 1/1971 | Courvoisie et al. | 73/61.62 |
| 3,627,493 | 12/1971 | Manley | 422/53 |
| 3,922,903 | 12/1975 | Bornstein et al. | 422/53 |
| 4,082,511 | 4/1978 | Bedford | 73/53.05 X |
| 4,267,148 | 5/1981 | Dickson et al. | 422/53 |
| 4,335,072 | 6/1982 | Barnett et al. | 422/53 |
| 4,497,200 | 2/1985 | Tournier | 73/53.05 X |
| 4,599,217 | 7/1986 | Winston et al. | 422/53 |
| 4,683,035 | 7/1987 | Hunt et al. | 436/6 X |
| 4,733,556 | 3/1988 | Meitzler et al. | 73/64 |
| 4,849,361 | 7/1989 | Dickakian | 436/2 |
| 4,966,032 | 10/1990 | Takeuchi | 73/64 |
| 4,967,035 | 10/1990 | Liljenfeldt et al. | 73/116 |
| 5,068,196 | 11/1991 | Hays et al. | 422/53 |
| 5,101,658 | 4/1992 | Wilson, III et al. | 73/61.2 |

Primary Examiner—James C. Housel
Assistant Examiner—Harold Y. Pyon
Attorney, Agent, or Firm—Kenneth H. MacLean

[57] ABSTRACT

An apparatus for testing engine lubricating oil under simulated engine operating conditions including a tank with an interior space containing a quantity of engine lubricating oil, an elongated tubular enclosure for passing oil from one end to the other, and an oil pump to cause oil to flow from the tank through the tubular enclosure. The tank includes devices to introduce oil oxidizing agents to the oil. A metal rod extends centrally through the enclosure so that oil passes along its outer surface and the rod is selectively heated so that oxidation deposits form along the rod. Examination and analysis of the rod and its deposits permit rating of a particular oil for its oxidation resistant properties.

7 Claims, 1 Drawing Sheet

THERMO-OXIDATION ENGINE OIL SIMULATION TESTING

BACKGROUND OF THE INVENTION

1. Field of the Invention

The subject invention relates to an apparatus and a method for testing oxidation resistant properties of lubricating oils for internal combustion engines and particularly turbocharged internal combustion engines. In a normal engine, the oil is exposed to relatively high temperatures and containments which can induce oxidation of the oil. A turbocharged engine, in addition, exposes the oil to the very high temperatures of the turbocharger shaft. When a hot engine is shut-off, the temperature of the turbocharger increases dramatically. Oil contacting very hot portions of the turbocharger can be rapidly oxidized and produce undesirable deposits on the internal metal surfaces. It can be understood that it is desirable to test oil under conditions simulating a hot engine.

The subject apparatus and method evaluates the oxidation resistant qualities of various oils under simulated engine and turbocharger conditions. The apparatus includes a reservoir holding a quantity of oil which is heated and exposed to contain such as moist air and nitrous oxide. These contaminants can cause formation of certain partially oxidized precursors which in turn can lead to deposit formation. The oil is pumped from the reservoir to a depositor apparatus which includes a heated rod over which the oil flows. Contact between the oil and the heated rod simulates the contact of hot oil with a turbocharger shaft of an engine. The temperature of the heated rod varies along its length due to the cooling effect of oil flowing along and over thereof. Deposits of oxidized products are formed on the surface of the rod and the quantity of the deposit can be determined by differential weight method. Also the appearance of the deposits can be studied to evaluate the oxidation resistance of lubricating oils.

2. Description of Related Art

There are several tests which are commonly conducted on lubricating oil to determine the oxidation effects of heating the oil. Equipment is available to perform infra-red spectra analysis on lubricating oils to detect various oxidation products. Other equipment is available to do a metals analysis or content on the oil. Neither of these tests very accurately reflects the environment of a hot engine and particularly a turbocharged engine.

It is known to test lubricating oil by passing lubricating oil over a heated rod. To a degree, this simulates an engine environment. However, it does not provide the two-stage thermal/oxidation effects of the subject apparatus and method. First, the subject apparatus and method uses an oil reservoir simulate to oil in an engine oil pan. The oil in the reservoir is heated and exposed to containments such as moist air and other oxidizing agents such as nitrous oxide. Secondly the contaminated oil is passed over a heated rod to stress the oil which tends to produce oxidation deposits on the rod. Applicant knows of no other test apparatus and method which provides such a two-stage thermal oxidation for lubricating oil as explained in more detail hereinafter.

SUMMARY OF THE INVENTION

The subject apparatus and method evaluates the oxidation resistent qualities of various oils and is particularly well suited for evaluating engine lubricating oils. The oil in a engine pan is exposed to relatively high temperatures and also to containments which tend to oxidize the oil particularly at higher temperatures. Moisture and various byproducts of gasoline enter the crank case of an engine and mix with the oil. It is known that these conditions in the oil pan tend to form certain partially oxidized products which are procures to formation of deposits particularly on hot surfaces of the engine. The shaft of the turbocharger is one of the hotter surfaces to which oil is applied. The engine's oil pan acts on the oil and carries out a reaction stage. When the partially oxidized oil from the pan is pumped to a hot area of the engine such as the shaft of the turbocharger, these partially oxidized products or procurers further oxidize and form deposits on the hot metal. The deposits resemble varnish, hardened sludge or ashen appearing substances.

It is desirable to evaluate oils of the basis of their oxidation resistent qualities under engine-like conditions. The subject apparatus and method permits evaluation by simulating the atmosphere and conditions of an engine for lubricating oil. The reservoir simulates the engine oil pour. The oil is further pumped to a hot component to simulate a turbocharger for example. The apparatus includes a heated rod over which oil flows and on which oxidized products of the oil are deposited. The quantity of these deposits can be determined by a differential weighing process (weighing before and after the test). The temperature along the rod varies depending on the distance from the oil inlet. Much can be learned about the oils oxidization resistent qualities by the appearance and position of the deposit on the heated rod. Varnishes, hardened sludges and ashen appearing deposits are formed along the rod. Thus the range of deposits on the rod presents a kind of thermal-gram of the different temperature encountered by the oil along the rod.

It has been found that the subject apparatus and method for evaluating oils for their oxidation resistent qualities is repeatable from test to test. Further, the apparatus and method is suited to the addition of other test methods such as infra-red spectra analysis or a metals analysis.

Further advantages of the subject apparatus and method will be more apparent by reference to the following detailed description of an embodiment, reference being to the drawings hereof of a preferred embodiment.

IN THE DRAWINGS

FIG. 1 is a somewhat schematic elevational and section view of the test apparatus; and FIG. 2 is an enlarged and sectioned view of a deposit formation assembly of the test apparatus shown in FIG. 1.

DETAILED DESCRIPTION OF A PREFERRED EMBODIMENT

Figure 1:
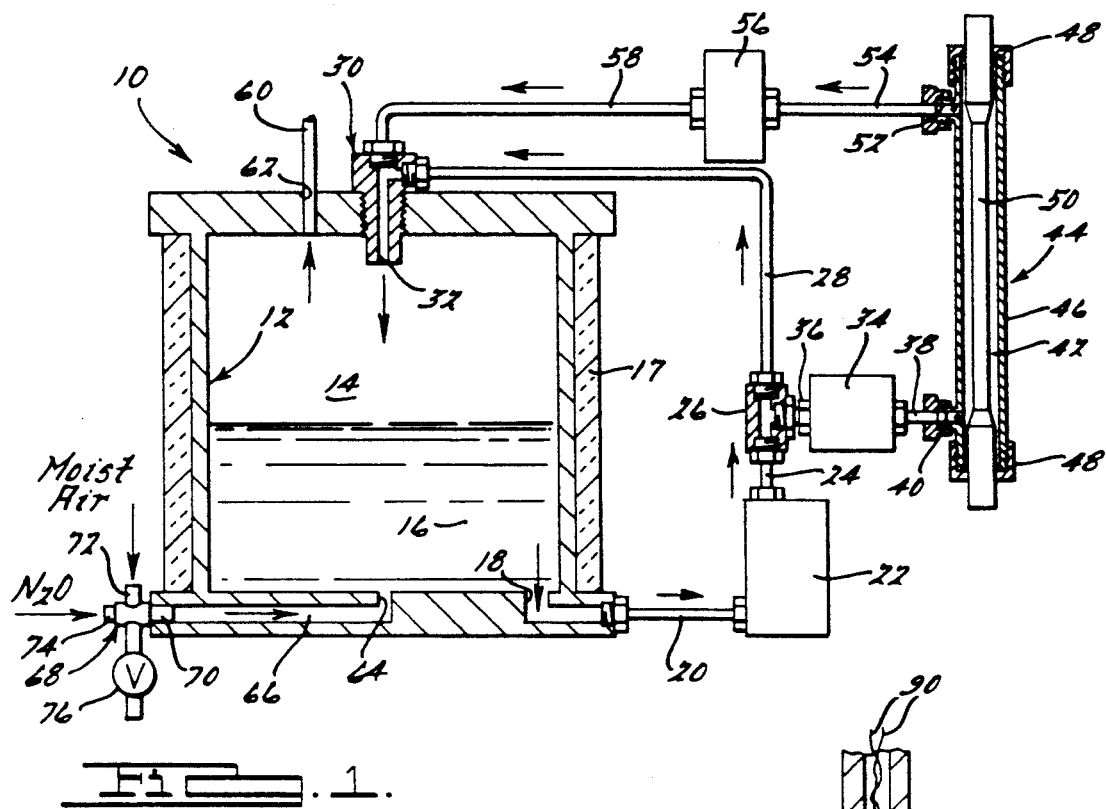

In FIG. 1, the test apparatus or engine simulation oil testing apparatus 10 is shown. Apparatus 10 includes a reactor vessel or enclosure 12 having interior space 14. A quantity of lubricating oil 16 partially fills space 14. A combination heater and insulating mantle 17 encircles the reactor vessel 12 to maintain the temperature of the oil 16 at a desired level corresponding to a typical oil temperature in an internal combustion engine, typically above 95 degrees centigrade.

The reactor enclosure 12 has an outlet passage 18 near its bottom portion for withdrawal of oil from interior 14. A conduit 20 connects outlet 18 to the inlet of a pump 22. A conduit 24 connects the outlet of pump 22 to a three-way fitting 26 having an inlet and two outlets. One of the outlets is connected by a conduit 28 to another fitting 30 which extends through the upper wall of the reactor enclosure 12 and serves as an inlet for the return of oil into space 14.

The other outlet of connector 26 is connected to a micro-meter valve 34 by a connector 36. The valve 34 in turn is connected by a conduit 38 to an inlet passage 40 leading to the interior 42 of a depositor assembly 44. The depositor assembly 44 has an outer cylindrical member 46 with upper and lower threaded end fittings 48 which removably attach thereto. A tubular metal rod 50 extends through the interior 42 and also through the end fittings 48. An annular passage is formed between the outer cylinder 46 and the rod 50 through which oil is pumped. An outlet passage 52 is formed at the upper end of the depositor assembly 14. At the upper end of assembly 44, a passage 52 is connected by conduit 54 to a filter 56. In turn, filter 56 is connected by a conduit 58 to the inlet fitting 30 to interior space 14.

The interior 14 of the reactor vessel 12 is vented by conduit 60 which defines a passage 62. An inlet is located passage 64 at the bottom portion of the reactor enclosure 12 to introduce containments such as moist air or nitrous oxide to the oil 16. The containments flow to inlet 64 through a passage 66 which is connected to a fitting 68. Fitting 68 has an inlet 70 connected to passage 66 and inlets 72, 74 connected respectively to a source of moist air and to a source of nitrous oxide. Further, a valved drain passage 76 is provided so that the contents 16 of the enclosure 12 can be drained.

Figure 2:
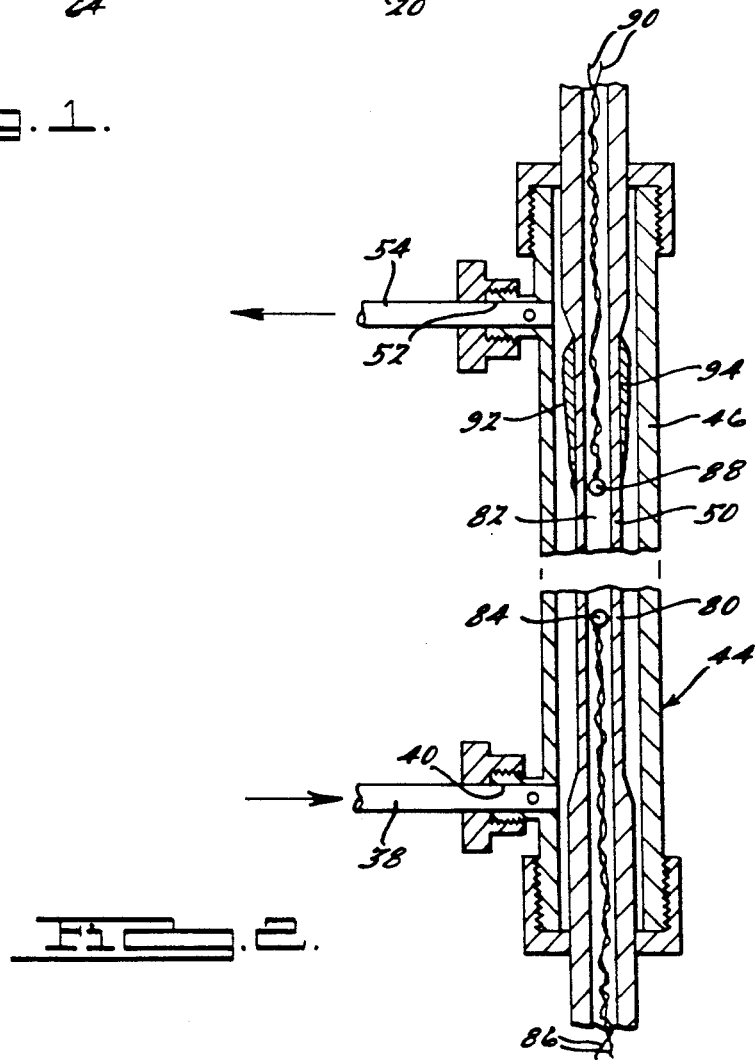

FIG. 2, illustrates details of the depositor assembly 44. Metal rod 50 has an outer cylindrical surface 80 located between inlet 40 and outlet 52. Pump 22 causes oil to flow over and along rod surface 80 at a rate determined by the micro-meter valve 34. The valve 34 allows the pump to operate at full capacity and bypasses most of the oil into conduit 28 and back to the interior 14 in bypass relation to the depositor assembly 44. During a test, the metal tube 50 is heated by electrical induction. This temperature is reflected within interior 82 of the tube 50. An oil inlet thermalcouple 84 is placed within the interior 82. Electrical leads 86 extend out from the lower end or the tube 50. Another thermalcouple 88 is positioned upward from thermalcouple 84 and has leads 90 which extend from the upper end of the tube 50. The difference between the thermalcouple outputs is used by an associated control and software program to control the temperature of the rod at a desired level. Thermal couple 88 also acts as a maximum temperature control to shut-off the electrical induction heating when portions of the rod exceed a maximum temperature.

The outer surface 80 of the rod 50 and in particular the upper surface 14 tends to receive formations of oxidized oil product or carbonyls. The thickness of these deposits build up as indicated by numeral 92. The deposit formation 92 insulates the portion of the rod thereunder from the cooling affect of oil flowing thereby and eventually that portion of the rod exceeds the maximum temperature allowed by thermal couple 88. At that time, the thermal couple 88 signals the associated control to terminate heating of rod 50 and thus signals the end of the test.

At the end of the test, the oxidized oil in interior 14 can be drained through valved drain passage 76. The filter 56 can be removed and examined for particles of oxidized products which were not deposited on the rod 50. In addition, the end caps 48 are removed from the cylinder 46 and the rod 50 carefully removed from the interior 42. The rod is then accurately weighed and the extent of the deposit 92 is determined by subtracting the pre-test weight of the rod. Also, the appearance of the deposits 92 reveals a variation of varnish, hardened sludge and ashen appearing deposits along its length with the ashen deposits appearing closer to the outlet passage 52 where the temperature of the rod is greatest.

TEST PARAMETERS

As previously mentioned, the reactor enclosure 12 simulates the oil pan and interior of an internal combustion engine in which a quantity of lubricating oil 16 is heated an exposed to various contaminants such as moist air and oxidizing gases from the fuel and products of combustion. These fuel related contaminants act as oxidizing agents and have the same affect on oil as does nitrous oxide. The oil 16 in the enclosure 12 is heated by an insulated mantle 17 to a temperature simulating the temperature of oil when operating engine, such as 95 degrees centigrade. The pump 22 withdraws some of the oil and pumps a portion of it into the depositor assembly 44.

The heating of rod 50 is cycled to simulate the conditions of a turbocharger when an engine is operating and when a hot engine is deactivated. Upon deactivation, the temperatures of the engine and turbocharger increase substantially and this is the worst condition to which oil is exposed.

A typical test uses about 100 millimeters of oil in the reactor enclosure. The valve 34 controls the flow rate of oil through the depositor assembly 44 at 0.46 millimeters per minute Moist air and nitrous oxide are introduced into interior 14 at a rate of 20 ccs per minute. The temperature of lubricating oil in the reactor is maintained at 95 degrees centigrade. A typical heating cycle for the rod 50 is as follows: First, the rod is heated to 150 degrees centigrade and held at that temperature for one minute. The rod is then increased in temperature to 500 degrees centigrade and held at 500 degrees centigrade for two minutes. The rod is then decreased in temperature to 150 degrees centigrade and held at that temperature for 24 minutes. The entire cycle takes 30 minutes. The cycle is repeated many times.

At the end of the test, the oil is drained from interior 14 and analyzed. The rod 50 is removed and weighed to determine the deposit quantity. The rod is also visually analyzed to determine deposit quality. In addition, materials collected by the filter can be studied and/or weighed.

Although one embodiment of apparatus for oil testing is shown and described for performing a specific testing method, it is contemplated that there may be modifications which still fall within the inventive scope as defined by the claims.

What is claimed is as follows:

1. Apparatus for testing engine lubricating oil under simulated engine operating conditions, comprising: oil storage means defining an interior space for containing a quantity of engine lubricating oil; an elongated reactor enclosure with and inlet at one end and outlet at an opposite end for passage of said oil therethrough; means for pumping oil from the storage means to the reactor means and subsequently back to the storage means; a metal rod extending through the interior of the elongated reactor enclosure so that oil passes along its outer surface; means to introduce oxidizing agents to said oil; heating means for the metal rod whereby oil in the oil storage means is mixed with an oxidizing agent to develop partially oxidized products and is then passed into contact with the heated metal rod causing formation of oxidized products which are deposited on the surface of the metal rod for subsequent study.

2. Apparatus for testing engine lubricating oil under simulated engine operating conditions, comprising: a storage tank defining an interior space for containing a quantity of engine lubricating oil, the tank having an inlet and outlet; an elongated reactor enclosure defining an interior and having an inlet at one end and an outlet at an opposite end; a pump for selectively passing oil from the storage tank to the reactor enclosure and back to the storage tank; a metal rod with an outer surface and extending centrally through the interior of the reactor enclosure so that oil passes along its outer surface; means to introduce oxidizing agents into said oil in the storage tank; heating means for the depositor rod whereby oil from the storage tank mixed with oxidizing agents contacts the heated metal rod and forms oxidized oil products which are deposited on the outer surface of the metal rod for subsequent study.

3. The apparatus as in claims 1 or 2 in which moist air as an oxidizing agent is introduced to the oil in the storage tank.

4. The apparatus as in claim 2 in which nitrous oxide as an oxidizer is introduced to the oil in the storage tank.

5. The apparatus as in claim 2 in which the metal rod is tubular with a hollow interior; at least one temperature sensor is positioned in the interior of the metal rod to monitor temperature.

6. The apparatus as in claim 2 and further comprising a filter positioned between the reactor enclosure and the storaqe tank to capture oxidized products formed adjacent the metal rod but shed therefrom.

7. The apparatus as in claim 2 and further comprising a bypass apparatus downstream from the pump to selectively pass a portion of the pump output directly back to the storage tank and the remainder to the reactor enclosure.

* * * * *